United States Patent
Birmingham et al.

[11] Patent Number: 6,010,554
[45] Date of Patent: Jan. 4, 2000

[54] MICRO-MACHINED VIRTUAL IMPACTOR AND METHOD OF OPERATION

[75] Inventors: Joseph G. Birmingham, Richland; Patricia M. Irving, Kennewick; Yin-Fong Su, Richland; Charles J. Call, Pasco, all of Wash.; Bruce D. Lerner, Bel Air, Md.; Robert S. Wegeng, Richland, Wash.

[73] Assignees: Battelle Memorial Institute; MesoSystems Technology, Inc., both of Richland, Wash.

[21] Appl. No.: 08/880,355

[22] Filed: Jun. 23, 1997

[51] Int. Cl.[7] .................................................. B01D 45/08
[52] U.S. Cl. ................................. 95/32; 55/444; 55/446; 55/463; 55/464; 95/267
[58] Field of Search ........................ 55/442–446, 463, 55/464; 95/31, 32, 267

[56] References Cited

U.S. PATENT DOCUMENTS

| | | | |
|---|---|---|---|
| 877,460 | 1/1908 | Brunner et al. | 55/444 |
| 902,958 | 11/1908 | Galusha | 55/444 X |
| 906,083 | 12/1908 | Terry | 55/444 X |
| 1,603,878 | 10/1926 | Smith | 55/444 X |
| 1,807,378 | 5/1931 | Budil | 55/444 |
| 1,825,274 | 9/1931 | Leach | 55/444 X |
| 2,939,545 | 6/1960 | Silverman | 55/444 X |
| 3,693,457 | 9/1972 | Pilat | 73/28 X |
| 3,754,868 | 8/1973 | Witz et al. | 210/216 X |
| 3,901,798 | 8/1975 | Peterson | 209/143 |
| 3,932,151 | 1/1976 | Lau | 55/444 X |
| 3,983,743 | 10/1976 | Olin et al. | 55/270 X |
| 4,133,202 | 1/1979 | Marple | 55/270 X |
| 4,321,822 | 3/1982 | Marple et al. | 55/270 X |
| 4,387,603 | 6/1983 | Nelson | 73/863.22 |
| 4,452,068 | 6/1984 | Loo | 73/28 |
| 4,640,140 | 2/1987 | Burghoffer et al. | 73/863.22 |
| 4,670,135 | 6/1987 | Marple et al. | 209/145 X |
| 4,689,052 | 8/1987 | Ogren et al. | 55/338 X |
| 4,697,462 | 10/1987 | Daube, Jr. et al. | 55/528 X |
| 4,764,186 | 8/1988 | Langer | 55/443 X |
| 4,767,524 | 8/1988 | Yeh et al. | 209/143 |
| 4,877,430 | 10/1989 | Gutermuth | 55/446 X |
| 4,941,899 | 7/1990 | Liu | 55/429 X |
| 4,942,297 | 7/1990 | Johnson et al. | 250/304 |
| 4,990,740 | 2/1991 | Meyer | 239/343 X |
| 5,040,424 | 8/1991 | Marple et al. | 73/863.23 |
| 5,128,539 | 7/1992 | Rodgers et al. | 250/255 |
| 5,254,861 | 10/1993 | Carpenter et al. | 250/573 |
| 5,318,609 | 6/1994 | Kittler | 55/445 X |
| 5,332,550 | 7/1994 | Booker | 422/83 |
| 5,412,975 | 5/1995 | Raabe et al. | 73/28.04 |
| 5,425,802 | 6/1995 | Burton et al. | 95/32 |
| 5,472,645 | 12/1995 | Rock et al. | 261/79.1 |
| 5,498,271 | 3/1996 | Marple et al. | 55/321 |
| 5,512,216 | 4/1996 | Rock et al. | 261/79.1 |
| 5,533,406 | 7/1996 | Geise | 73/863.22 |

FOREIGN PATENT DOCUMENTS

| | | |
|---|---|---|
| 0 543 108 A1 | 5/1993 | European Pat. Off. . |
| 626 191 | 8/1927 | France . |
| 13 10 913 | 9/1934 | Germany . |
| 1310913 | 9/1934 | Germany . |
| 2 260 729 | 5/1974 | Germany . |

OTHER PUBLICATIONS

Vance, Richard F., "Slanted Baffle Mist Eliminator"; *U.S. Statutory Invention*; Registration No. H1499; Nov. 7, 1995.
Patent Cooperation Treaty Search Report, PCT/US98/12471; Corona Catalysis Corporation et al.; Oct. 14, 1998.

*Primary Examiner*—Richard L. Chiesa
*Attorney, Agent, or Firm*—Stephen R. May; Jeffrey M. Sakoi

[57] ABSTRACT

A micro-machined virtual impactor device to permit the separation, collection and concentration of a significant portion of environmental particulates having a diameter of less than ten microns and its method of operation. The device includes a plurality of projections, each having a virtual impact surface that defines an aperture in a stagnant zone of fluid flow. A major portion of the particulate material is concentrated into a minor portion of the fluid which is processed through the aperture, where it is collected for subsequent analysis.

30 Claims, 10 Drawing Sheets

MICRO-MACHINED VIRTUAL IMPACTOR AND METHOD OF OPERATION

This invention was made with Government support under Contract DAAM01-97-M-0006 awarded by the U.S. Department of Defense. The Government has certain rights in this invention.

BACKGROUND OF THE INVENTION

The capture of particulate matter or aerosols in air or other fluid streams is of concern in two entirely different contex: first, as an analytical tool to determine the type and concentration of such particulate/aerosol material, and secondly as a method of cleansing the fluid stream for subsequent use. Additionally, there are occasions in either case where classification of particulate matter by size is desired. For example, the detection of airborne biological or chemical warfare agents, the detection of biological contamination in confined spaces such as aircraft or hospitals or the detection of industrial pollutants (either in ambient air or in stacks) may be required in various and different scenarios.

Much effort has been expended in the past in the detection and classification of particulate matter or aerosols, generally in air or other gaseous streams. Impactors have been used for collecting aerosol particles for many decades. In the earliest embodiments, a stream of gas containing the particles was accelerated towards an impactor plate. Due to their inertia, the particles hit the receptor plate and were collected there while the gas deflected to the side. Therefore, only heavy particles were collected while particles below a "cut-off threshold" size were carried away by the air stream. This concept has been refined over the years, as in U.S. Pat. No. 3,901,798, wherein suspended particles in an air stream are caused to flow along a path having one or more sharp turns. Smaller particles with less mass and inertia negotiate the turn and continue along the deflected path for detection. Larger particles with greater mass and inertia fail to negotiate the turn and continue along the original direction for separation and/or detection.

However, a significant cause of inaccuracy in such impactors results from the deposition of particles on surfaces of the impactor other than the intended collection surfaces. This phenomenon reduces the slope of the particle collection efficiency curves for the impactor stages and reduces the accuracy of measurement of total particle mass concentration and of the size-fractionation of particles since such losses cannot be accurately estimated for aerosols having varying size, shape or chemistry. Additionally, particles may either reentrain in the airstream or bounce from the collection surface upon impact.

To remedy this problem "virtual" impactors have been developed that separate particulate matter in a fluid stream by forces other than impaction, and hence reduce the inaccuracies induced by particle deposition on the device. These devices may operate on a number of different principles, but all avoid actual "impact" and all virtual impactors rely on differences in mass to induce inertial separation. In such devices, the particulate-laden fluid stream (generally air or other gas) is directed toward a surface presenting an obstruction to the forward movement of the fluid stream. In a laminar flow device, the particles are carried along in the air stream with the air molecules, but when the air changes direction (to avoid the obstruction), the heavier particulate matter will be separated from the main portion of the air stream. A region of relatively stagnant air (a "dead air zone") is created in the air stream, comprising a minority of the air stream, but which contains a majority of the particulate matter. The "virtual impact surface" is formed when the air stream separates into major and minor flow streams, such that fine particles remain entrained in the deflected major portion of the air stream, while more dense particles with greater inertia remain in the stagnant air zone in the minor portion of the air stream, where they can be captured.

Because many of the prior art virtual impactors did not actually collect particles themselves, but merely redirected them into two different air streams according to their mass, they were essentially free of the problems of particle bounce and reentrainment associated with actual impact devices.

Virtual impactors have been devised in a number of embodiments. For example, U.S. Pat. No. 4,670,135 discloses a plurality of virtual impactors each having an inlet nozzle and a receiving tube arranged on a housing or frame for parallel flow and which are utilized to obtain a high flow rate while keeping the flow rate through each individual virtual impactor at a reasonable value. Similarly, U.S. Pat. No. 5,425,802 discloses a s virtual impactor with a nozzle for accelerating an entering airstream, particle receiving means positioned downstream from the nozzle means, and a chamber in fluid communication with the gap between the nozzle means and the receiving means.

In an effort to enrich gases with aerosol particles to certain orders of magnitude for purposes of classification, the virtual impactor of U.S. Pat. No. 5,533,406 comprises a generator plate with an inlet side and outlet side, with a receptor plate disposed parallel with the generator plate so as to define a space therebetween, with each having at least one nozzle in the form of a slit which is curved to form a closed loop. Classification of aerosol particles is also provided by U.S. Pat. No. 3,901,798, wherein a first plate defines a first orifice, and a second plate spaced from and downstream from the first plate defines a second orifice larger than and substantially concentrically disposed with respect to the first orifice. Tubular means in the plane of the second orifice defines a third orifice and an annular passage between the second orifice and tubular means.

A dichotomous virtual impactor is disclosed in U.S. Pat. No. 4,767,524, wherein an impaction plate is replaced by a region of stagnant air in a receiving probe. A virtual surface is formed by deflected streamlines that are similar to those in conventional solid plate impactors. The fine particles follow the streamlines of the major air flow, while the coarse particles pass into the forward minor flow region.

As is apparent from a review of the prior art, the technology of virtual impactors is well known, and advances in the art are occasioned by new designs creating more efficient or more specific separations. The apparatus of the present invention accomplishes both.

BRIEF SUMMARY OF THE INVENTION

The present invention comprises an apparatus for separation and concentration of particulate matter from a fluid stream. It is contemplated that the fluid stream may comprise either a gaseous or a liquid, and the particulates may be aerosols, suspended solid matter, microscopic biological material, or the like. The invention may find particular application in the environment of battlefield biological warfare agents, but may be equally useful in the detection and classification of industrial or environmental particulates. Uses in other defense-related areas, for detection of terrorist activities, and in public health arenas are also contemplated.

The invention comprises an apparatus to direct the fluid of interest into the device, either in the form of a pump or vacuum. The collected fluid is directed through an inlet port and across a plurality of individual virtual impact components. In various embodiments, the virtual impact components present either a convex or concave obstruction to the advancing fluid stream, but in any case create a "dead" zone where particulate matter tends to settle out, while the majority of the fluid stream changes direction and flows around the obstruction. An aperture is provided such that particulate matter in the minor portion of the fluid stream, in the dead zone, are directed through the aperture and to a collection area where they are entrained in a separate fluid for eventual analysis.

The device directs a minor portion of the fluid stream through the apertures, but such minor fluid portion contains a major portion of the particulate matter. For example, for a given quantity of the fluid stream entering the device, 10% of the fluid stream may be directed through the apertures and to the collection area, and may contain up to 90% of the particulate matter in that given quantity of the fluid stream.

The apparatus of the present invention may take any one of a number of different configurations. For example, the device may comprise: (I) a fluid inlet component in the form of an air supply plenum; (ii) a separation component in the form of a plate having a plurality of projections in the form of micro-virtual impact devices machined thereon; and (iii) a collection component in the form of a fluid in which the particulate matter for analysis is entrained. When assembled, air with the particulate of interest is forced through the air supply plenum, through the separation component, where a minor portion of the air stream is directed to the fluid in the collection component, whereupon the particulates are separated and concentrated for later analysis.

The apparatus of the present invention is not limited to any particular structural configuration. For example, the projections may be aligned in a number of adjacent parallel rows, or they may be aligned in a spiral, or any other shape wherein fluid flow around the projections can be controlled.

The present invention enables the collection of greater than 80% of particulate matter having a diameter of 1 micron.

BRIEF DESCRIPTION OF THE DRAWINGS

FIG. 1 is a schematic representation of first embodiment of the invention;

FIG. 2 is a sectional view of the embodiment represented by FIG. 1;

FIG. 3 is a schematic representation of the micro-machined virtual impactor devices illustrated in FIG. 1;

FIG. 4 is an alternative embodiment of the impactors illustrated in FIG. 1;

FIG. 4*a* is a sectional view of the impactors of FIG. 4;

FIG. 5 is a still further embodiment of the impactors of the present invention;

FIG. 6 is an exploded view of a schematic representation of a completed device of the present invention;

FIG. 7 is a plan view of the air inlet plate of the present invention;

FIG. 8 is a sectional view of the air inlet plate taken along lines 8—8 of FIG. 7;

FIG. 9 is a sectional view of the air inlet plate taken along lines 9—9 of FIG. 7;

FIG. 10 is plan view of the separation plate of the present invention;

FIG. 11 is a section view of the separation plate taken along lines 11—11 of FIG. 10;

FIG. 12 is a plan view of the particle collection plate of the present invention;

FIG. 13 is a sectional view of the particle collection plate taken along lines 13—13 of FIG. 12;

FIG. 14 is a longitudinal sectional view of the assembled device of FIGS. 7, 10 and 12;

FIG. 15 is a sectional view of the assembled device taken along lines 15—15 of FIG. 14;

FIG. 16 is an alternative embodiment of the present invention wherein the projections are arranged in a spiral pattern;

FIG. 17 is a specific embodiment of the projections of a prototype as set forth in the Example; and FIG. 18 is a graph of results from actual operation of the prototype device as set forth in the Example.

DETAILED DESCRIPTION OF THE INVENTION

As used hereinafter, the following terms shall have the following definitions:

"projection"—an obstruction having a vertical component placed in a fluid stream which forms a zone of stagnant air, serving as a virtual impact surface dividing the fluid stream into major and minor components for the separation of particulate matter entrained therein, without resulting in actual impaction between the particulate matter and the projection;

"particulate matter"—any separately identifiable solid, liquid, aerosol or other component entrained in a fluid stream which has a greater mass than the fluid forming the fluid stream, and is the subject of separation and collection for analysis;

"fluid"—any fluid susceptible to fluid flow, which may comprise liquids, or gases, and which may entrain foreign particulate matter therein. Unless otherwise noted, "fluid" shall mean the ambient fluid containing unconcentrated particulate matter for collection, not the fluid into which the particulate matter is concentrated after collection or capture.

In its broadest embodiment, the present invention comprises a separation component which utilizes the concept of massive parallel processing to place a plurality of extremely small vertical projections which create a zone of stagnant air in the path of a fluid stream, each one of which is capable of separating particulate matter from the fluid stream. When constructed in accordance with the present invention, the apparatus is capable of concentrating at least 80–90% of the target particulate matter into approximately 10% of the fluid stream. At the same time, air flow through the inventive apparatus can be as high as 100 L/min. for a separation component having, for example, 150 micro-machined projections, which is quite surprising given the small size of the collection components individually, and the entire apparatus.

The apparatus of the present invention permits flexibility in design sufficient to enable construction of devices to analyze virtually any flow rate in the fluid stream, by varying the number of projections on each separation component, and the number of separation components utilized. For example, a plurality of individual projections may be arranged on each separation component, and a plurality of separation components may be arranged in a single apparatus. By stacking 10 of the separation components (each with a throughput of 100 L/min), one may increase throughput of a single device to 1000 L/min of fluid sampled.

For example, assembling 10 of the 100 L/min separation components in a single device will provide 1000 L/min of fluid flow through the device. Operation of such device for 5 minutes ensures sampling of approximately 5000 L of fluid. If the ambient fluid has one particle of particulate matter per liter of fluid (a relatively low concentration), 5000 L will contain 5000 particles. 90% separation into 5 ml of collection fluid will yield approximately 4500 particles, or a concentration of 900 particles per ml., easily within the detection limit of a number of commercially available detection units.

Figure 1:
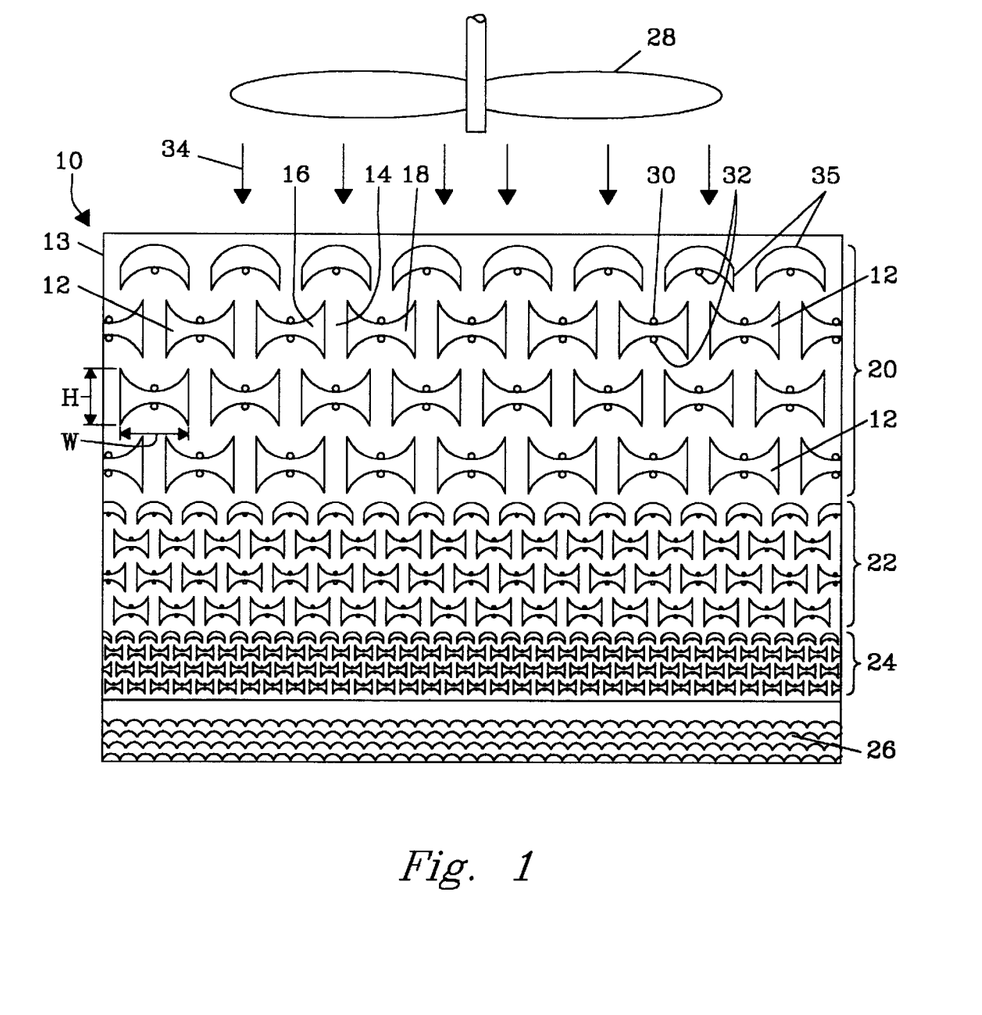
Figure 2:
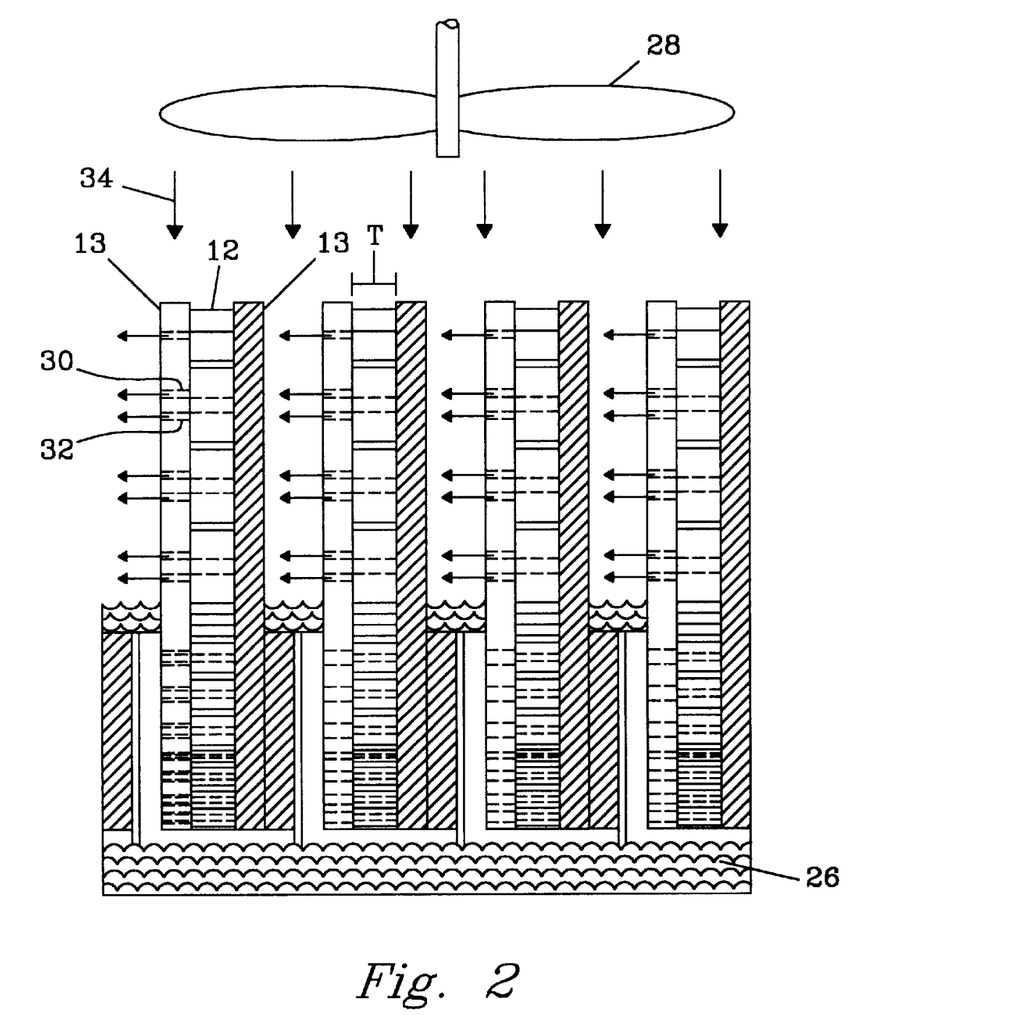

As illustrated in FIGS. 1 and 2, the apparatus 10 of the present invention comprises a plurality of individual projections 12 (butterfly shape) arranged in a plurality of different rows between plates 13. As arranged, the projections 12 are offset from one another such that fluid passageways 14 are provided between adjacent projections 16, 18. As illustrated in FIG. 1, the projections may be arranged such that they classify particulate matter by size (as described in greater detail below) by providing a plurality of projections of a first size arranged in rows 20 to collect larger particles, a plurality of projections of a smaller size arranged in rows 22 to collect smaller particles, and a plurality of projections of a still smaller size 24 to collect even smaller particles. In the schematic embodiment of FIG. 1, the device comprises a particulate collection portion 26 and a fan 28 (or other device, such as a vacuum pump) to move fluid 34 through the device. Each projection defines at least one aperture 30 designed to separate on the order of 80% of the particulate matter in that portion of the fluid stream to which that individual projection is exposed. The projections are designed to separate out from about 5% to about 40% of the air stream (fluid 34) exposed to an individual projection, and collectively, the aggregate of all the projections is designed to separate out about approximately 10% of the total fluid 34 entering the device. In the embodiment illustrated herein, a pair of apertures 30, 32 are provided for each projection 12. One of the apertures 30 is provided in an "upstream" side of the projection, while a second of the apertures 32 is provided on a "downstream" side of the projection. Collection efficiency may be improved by placing a plurality of vane projections 35 (crescent shape) at the fluid inlet, each vane projection 35 having a "downstream" aperture 30.

Figure 3:
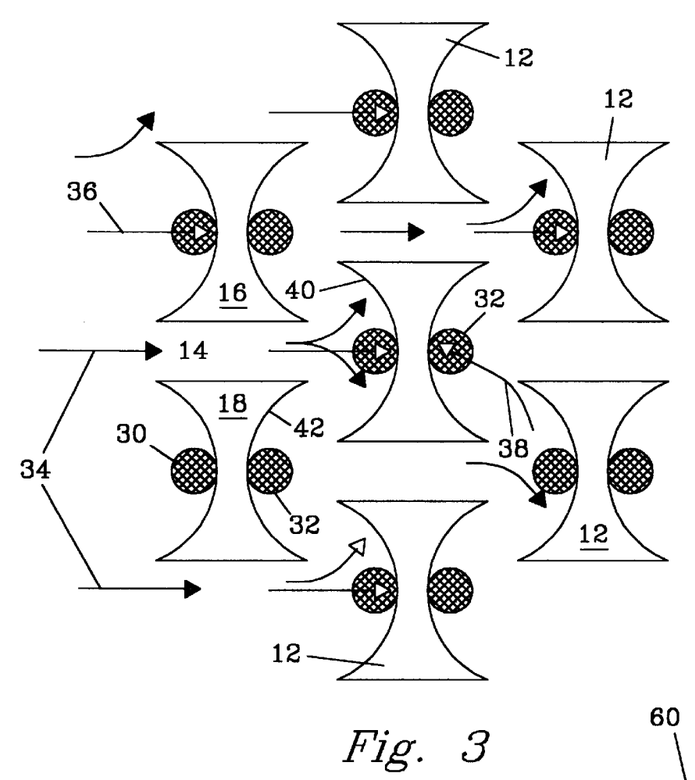

As illustrated in FIG. 3, adjacent projections 16, 18 define a fluid passageway 14 therebetween. A portion 36 of the fluid 34 is directed directly into each "upstream" aperture 30, while a second portion 38 of the fluid flow is directed into each "downstream" aperture 32. The concave upstream surface 40 of each projection 12 directs a portion of the fluid flow toward the downstream aperture 32 of adjacent projections, a minor portion of which enters the downstream aperture and a major portion of which is redirected by the downstream concave surface 42 to the upstream surface 40 of an projection in the next downstream row of projections.

The rows of projections are preferably arranged such that axes of apertures and axes of passageways between adjacent projections (as measured in the direction of fluid flow through the device) are alternated such that the axis of passageways in an upstream row is aligned with an axis of apertures in the immediately downstream row (and vice versa), thereby insuring that the flow of the fluid from one row to the next (from upstream to downstream) is maximally directed toward the apertures which lead to the collection component.

The fluid flow through the device of FIG. 1 separates entrained particulate matter with a "dead air" or quiescent zone created at the apex of each concave surface 40, 42 such that particulate matter above a predetermined mass settles out in these areas and is entrained in the minor portion of the fluid stream entering the apertures. The apertures direct the minor portion of the fluid stream, and the major portion of the particulate matter, to the collection point 26 for subsequent analysis.

It is to be understood that the fluid to be analyzed herein may be any fluid susceptible to having entrained particulate matter separated therefrom. While it is contemplated that the most likely use environment of the present invention will be detection of biological warfare agents in the form of aerosols in an ambient air stream, the device can be used in numerous other environments, such as collection of industrial pollutants in ambient air, collection of stack gases, sampling of air in buildings associated with "sick building" syndrome, collection of infectious or disease causing organisms in hospitals, and the collection of radioactive particles or toxic vapors. It is also contemplated that the apparatus may be used for the detection and collection of airborne particulate matter associated with illegal drugs or their precursors, and the collection of fluorescent particles in a liquid media used to test/calibrate this or similar devices.

Calculations of the efficiency of a device manufactured according to the schematic of FIG. 3 indicate that the collection efficiency of a device with apertures having 0.02" diameters is:

$$d_{50} = (9 \; u \; W \; St_{k50}/C_c \; v \; p)^{1/2} \quad (1)$$

where:

$d_{50}$=diameter of particle collected with 50% efficiency (m)

u=gas viscosity of air=$1.81 \times 10^{+5}$ kg/ms

W=width of micromachined virtual impactor aperture= 0.0005 (m)

V=gas velocity=2.3 m/s based on (100 L/min)(1 min/60 sec) (total area of all inlets=0.00008 m$^2$)

p=density of bioaerosol particulate=1000 kg/m$^3$ $St_{k50}$=Stokes number at the 50% collection efficiency=0.5

$C_c$=Cunningham Slip Correction factor=1. Therefore, the virtual impactor apparatus of the present invention has a calculated collection efficiency of greater than 50% for particulate matter having a diameter of greater than 0.5 microns. Applicant's experimental results support the conclusion that at least 80–90% of particulate matter having a diameter of 1 micron will be collected from the air stream sampled.

As illustrated in FIG. 1, the device of the present invention may be constructed such that particulate matter is classified by size. The device illustrated schematically in FIG. 1 will classify relatively smaller particles as the fluid stream progresses through the device, with the individual projections 12 and the apertures associated therewith becoming progressively smaller. A plurality of the separation components may be ganged together as illustrated in FIG. 2 to increase the throughput through the device.

Figure 4:
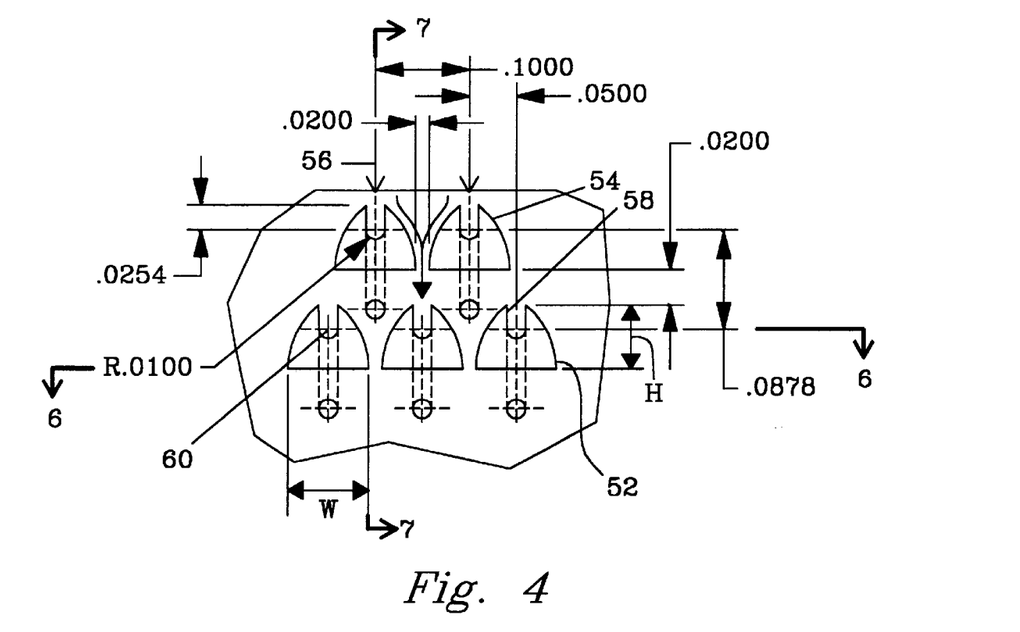
Figure 4A:
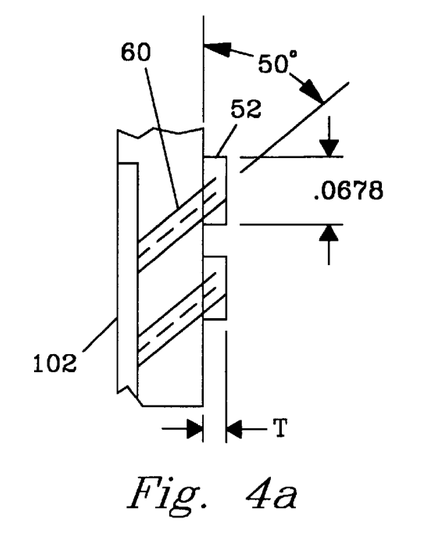

Refinements of the specific structure of the projections may include projections 52 (haystack shape) presenting a convex surface 54 to the advancing fluid stream 56, as illustrated in FIG. 4. Within the convex surface 54 is a concave portion 58 having the aperture 60 therein. Preferably, the concave portion 58 will be located at the apex of the convex surface, and the aperture 60 will be located adjacent the apex of the concave portion of the projection comprising the virtual impact surface. In the embodiment of FIG. 4, only the "upstream" side of the projection is a collector, unlike the double-sided collection of FIG. 1. Therefore, only a single aperture need be provided in the embodiment of FIG. 4. The dead air space created in the concave portion 58 is capable of settling out most particulate matter directed therein.

Figure 5:
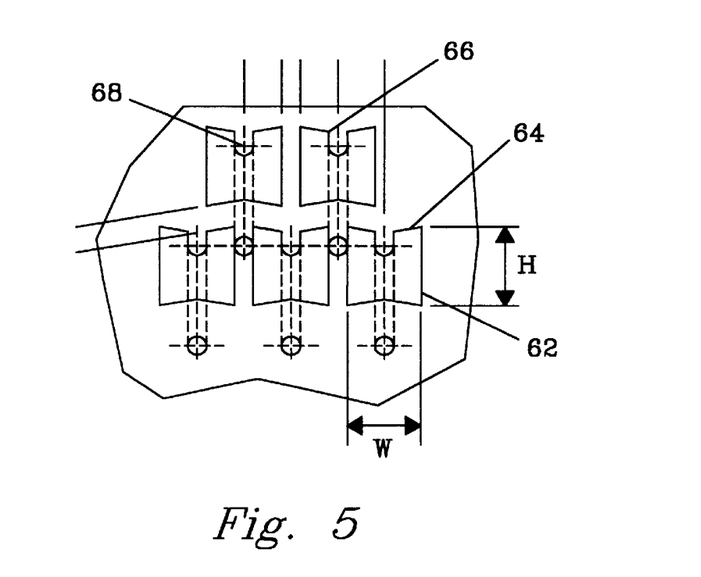

A still further alternative embodiment is illustrated in FIG. 5, wherein the projections 62 (tab shape) are provided with a high radius concave (or elliptical) virtual impact collector surface 64 facing upstream of the fluid flow. The surface 64 is provided with a concave portion 66 having an aperture 68 defined therein in the same manner as the projection 52 of FIG. 4.

The micro-machined virtual impactor devices of the foregoing figures are merely the operative portion that actually separate the particulate matter from the fluid stream. In practice, the projections must be provided a fluid stream and a means of collecting particulate matter. As illustrated schematically in FIG. 6, the particle separation plate 80 upon which the projections are machined is interfitted between a fluid inlet plate 82 and a particle collection plate 84.

Figure 7:
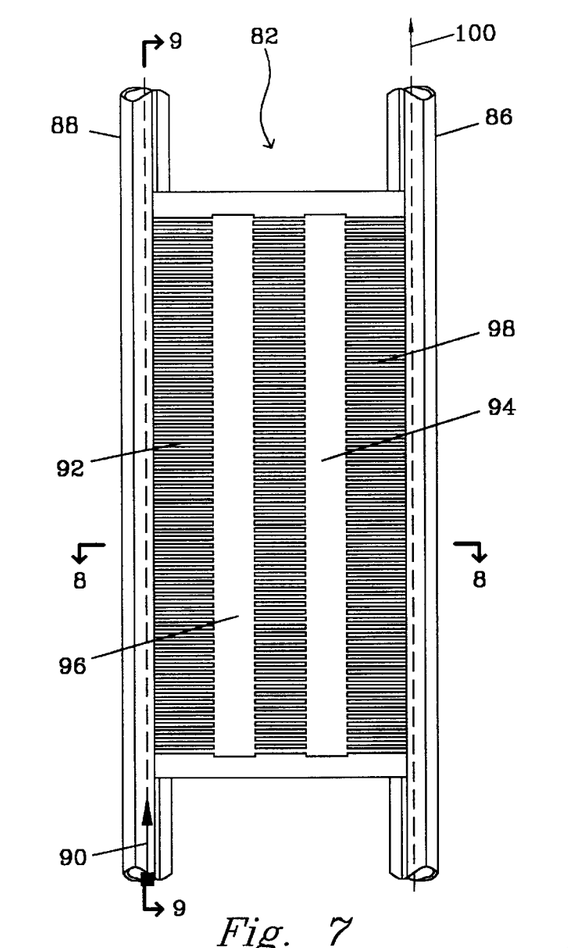
Figure 8:
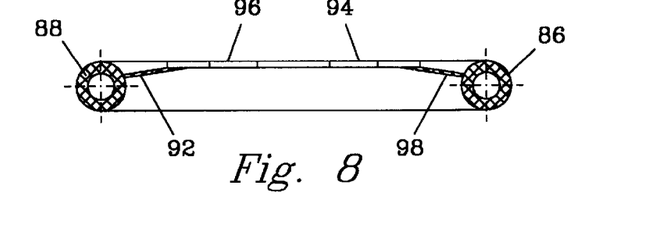
Figure 9:
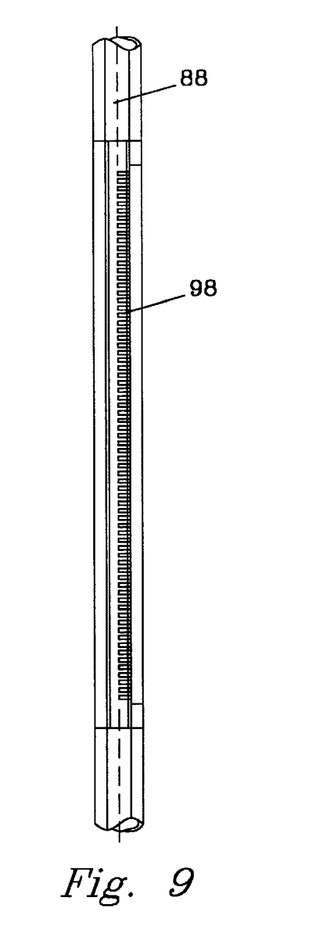

In a preferred embodiment for the sampling of an air stream, the air inlet plate (FIG. 7) is provided with a pair of air plenums 86, 88 to supply ambient air having a particulate of interest entrained therein to the device. The air plenums and an associated intake pump comprise a closed system to provide ambient air to the device under pressure. In the example of FIGS. 7, 8 and 9, air enters through plenum 88 (as at arrow 90) and proceeds along the length of plenum 88. Plenum 88 may be provided with a longitudinal slit, with a plurality of apertures, or any other convenient method of distributing the entering air stream to the device. As illustrated, the air stream exits the plenum and travels laterally through a plurality of grooves 92 to the separation component comprising the projections. The air flow laterally through grooves 92 is directed onto the projections (FIG. 10), which are positioned in a pair of troughs 94, 96 in the plate 82. The major portion of the air stream (containing a minor portion of the particulate matter) that is not directed to the particle collection portion of the device exits the separation plate 80 through a second set of grooves 98, and thence into the plenum 86 where it is exhausted from the device, as at 100.

In the view of FIG. 8, it can be seen that in the preferred embodiment, the air stream is directed through grooves 92, 98 as it enters and exits the devices. As set forth above, a major portion (for example, 90%) of the air stream entering at 92 will exit through grooves 98 and plenum 88.

Figure 10:
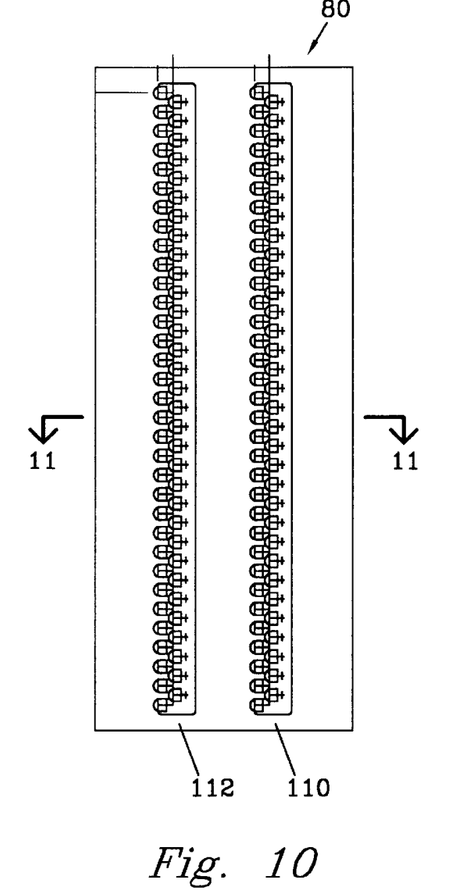
Figure 11:
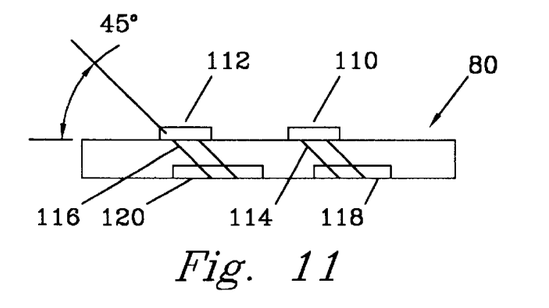

While the separation plate 80 may be provided with any number of projections thereon, as illustrated in FIG. 10, 11, four rows of projections are provided. As illustrated, the projections are arranged in two rows 110, 112 adapted to interfit with the troughs 94, 96 respectively. As noted above, each projection is provided with an aperture in the dead air zone, the aperture or channel 118, 120 being the "upper" terminus of a passageway 114, 116 provided through the thickness of the plate 80. The passageways may be provided in any convenient form, but Applicants have determined that the most acute angle possible is optimal. In practice, an angle of approximately 45° will suffice.

Figure 12:
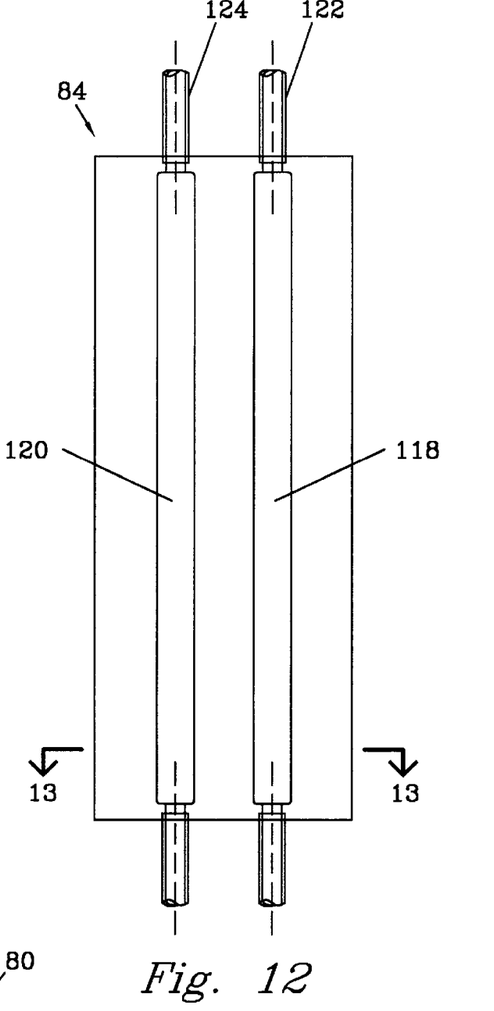
Figure 13:
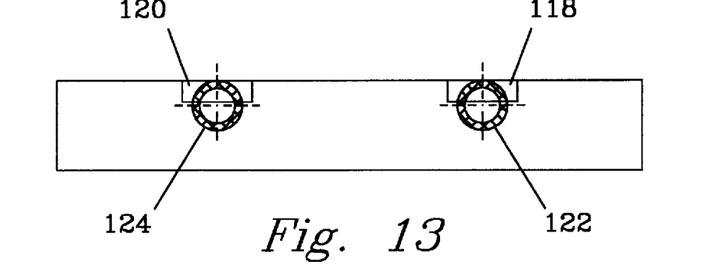

The particle collection plate 84 (FIG. 12, 13) is provided with a pair of channels 118, 120 milled into the plate that correspond with the passageways 114, 116 respectively. Each of the channels 118, 120 is interconnected with a fluid circulation means 122, 124 that provides fluid to the channels. While any convenient fluid may be circulated in the device, water may be the preferred fluid in many environments. The fluid circulation system is preferably a closed system, with a pump (not shown) to circulate the fluid through the channels as the minor portion of the air stream is directed into the fluid. Applicant has found that transfer of the particulate matter into the fluid is assisted if the fluid in channels 118, 120 wicks up a substantial portion of the length of passageways 114, 116 toward the apertures so that the positive pressure of the device forces the fluid entering the apertures to enter the water or other fluid in channels 118, 120.

Figure 14:
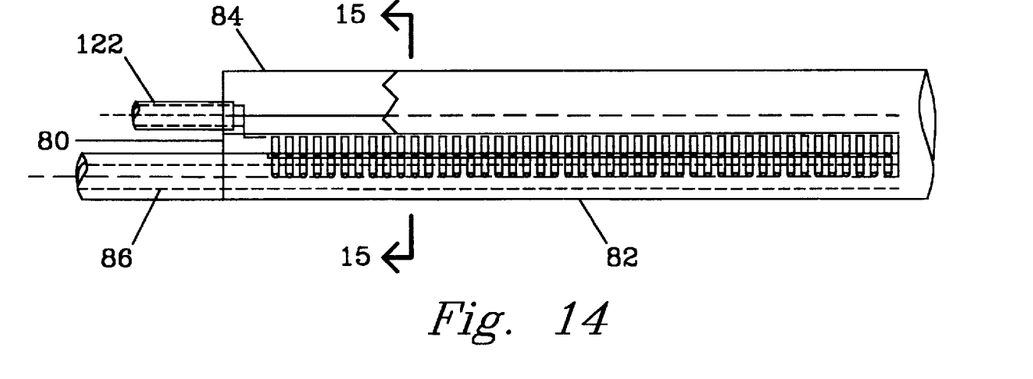

The assembled device is illustrated in FIG. 14. The three plates may be machined such that a simple film or layer of, for example, silicon gel, is sufficient to ensure air-tight integrity of the system. Or, raceways for gaskets may be machined in the plates to ensure integrity of the system. The three plates of the device are preferably secured to one another with screws (not shown in FIG. 14).

Figure 15:
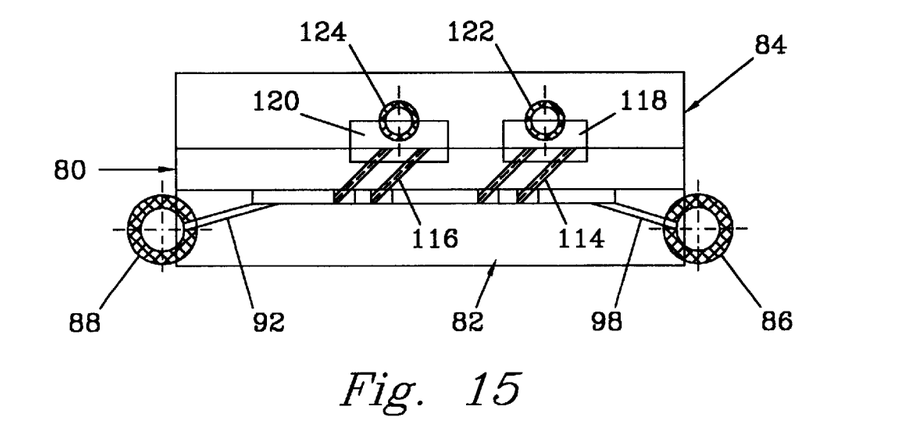

The sectional view of the device of FIG. 15 illustrates operation of the device. Ambient air containing particulate matter of interest enters the device at 88, and is directed through grooves 92, whereupon it is induced to flow toward the projections (micro-virtual impactors) 112 and 110. A major portion of the air stream is exhausted from the device through grooves 98 and plenum 86. A minor portion of the air stream is captured in the apertures 30, whereupon it is then directed through passageways 114, 116 to the fluid in channels 118, 120.

Figure 16:
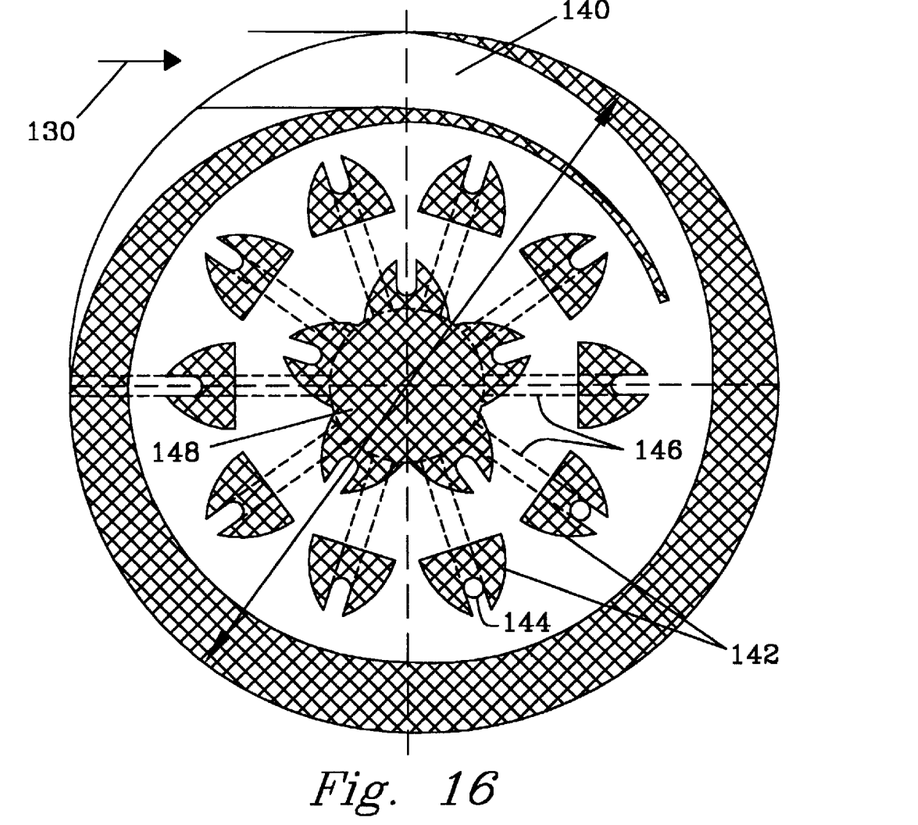

An alternative embodiment of the present invention is illustrated schematically in FIG. 16, which is a representation of a single device comprising a plurality of the projections described above. It is to be appreciated that a plurality of the separation plates 80 of FIG. 16 may be assembled one above the other to provide greater throughput. In this device, an air stream 130 is directed into the inlet 140 of the device, whereupon it is directed in a spiral motion to the plurality of projections 142 (similar to those illustrated in FIG. 4). The device of FIG. 16 acts as a "virtual centrifuge", such that an initial separation occurs prior to the particulate-laden gas stream reaching the projections, wherein relatively heavier particulate matter is separated toward the periphery of the device As illustrated, the projections 142 of FIG. 16 are arranged radially; it is to be understood that the orientation of the individual projections may be canted somewhat so that they face more into the advancing air stream. Each of the projections 142 defines an aperture 144, which is interconnected by passageway 146 to a central plenum 148. Each of the projections therefore feeds a minor portion of the air stream and a major portion of the particulate matter into the central plenum, from which analytical measurements may be made. The major portion of the air stream entering the device of FIG. 16 must be exhausted through an exhaust port (not shown).

The devices of the present invention may be provided for continuous measurement (for example, of particulate matter in a gaseous exhaust stream), or for batch measurement (as, for example, in a personal detector worn by a combatant exposed to biological warfare agents). The intended use will determine many of the particular structural features of the device, such as its size, amount of fluid flow (both air and liquid) through the device, and the like.

The analytical measurements made of, for example, the water/particulate stream of the device of FIG. 15, or the air stream of FIG. 16, may be made by any conventional analytical method. If in a continuous or batch mode, the sampled material may be distributed to one or more detectors. In either case, the analytical method chosen will be predetermined by the particular needs of the users.

EXAMPLE

Figure 17:
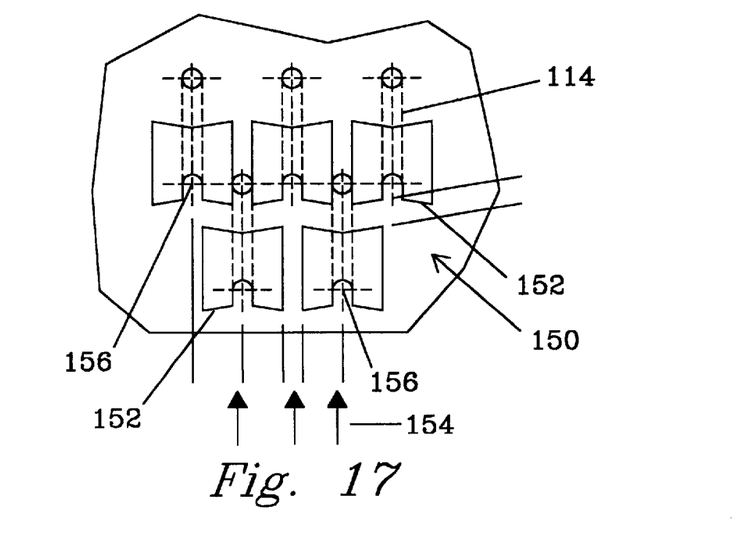

A device as illustrated herein was constructed, with the individual projections 150 comprising a "tab" shape (FIG.

Figure 6:
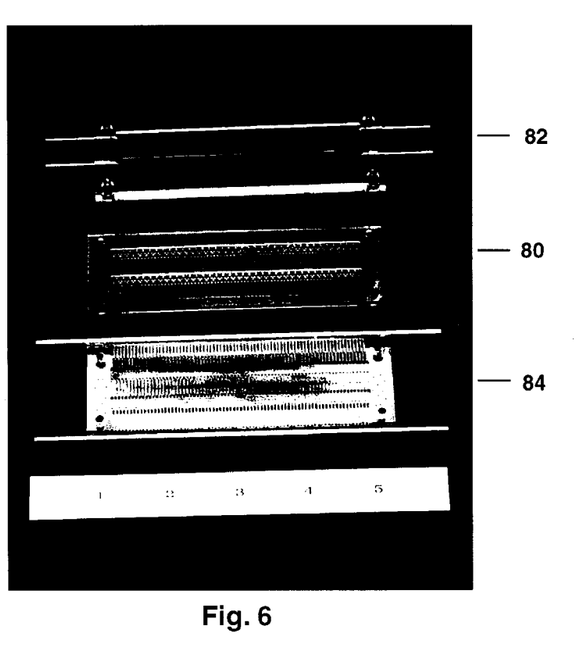

17). The projections were provided with a slightly concave surface 152 facing upstream into the advancing air stream 154. Apertures 156 were provided at the apex of the concave surface 152. The dimensions of the projections measured approximately 0.070"×0.080"×0.036" in height. Spacing between adjacent projections (both in the same row and in the next downstream row) was 0.020". The apertures measured 0.020" in diameter. The passageway from the aperture 156 to the fluid channel 118 was drilled at a 45° angle. Two double rows of projections were provided (as illustrated in FIG. 10) with 75 projections per double row (150 total projections). The remainder of the device was constructed as illustrated in FIG. 6. The overall dimensions of the device were 4.5" (length)×1.5" (width)×0.5" (thickness). Approximately 5 ml of water was used as the liquid in the collection component, and throughput of air was between 100–200 L/min.

Nebulizers were used to generate an aerosol with fluorescent polystyrene latex (PSL) microspheres. Ten different particle sizes ranging from 0.2 to 5.5 micron diameters were tested. The PSL solution was atomized in a Retec nebulizer with a 30 mL reservoir volume operating at 20 psig. Droplet sizes of 6 micron were produced. The flow rate of nebulizing air was between 2.5 and 3.0 L/min. Approximately 0.175 mL of the as received PSL solution was added to 30 mL of deionized water in the nebulizer. An average of 45 mL of this solution was used during each 30 minute experiment.

A condensation nuclei counter and laser particle measuring system were used to quantify particle size and concentration in the gaseous state, while a Coulter Counter and fluorometer were used for liquid phase samples. A Sequoia Turner model 450 fluorometer was used to measure fluorescence of liquid samples. Each standard solution was prepared by diluting 0.01 mL of as received 2.6% solids solution in 500 mL of deionized water.

Figure 18:
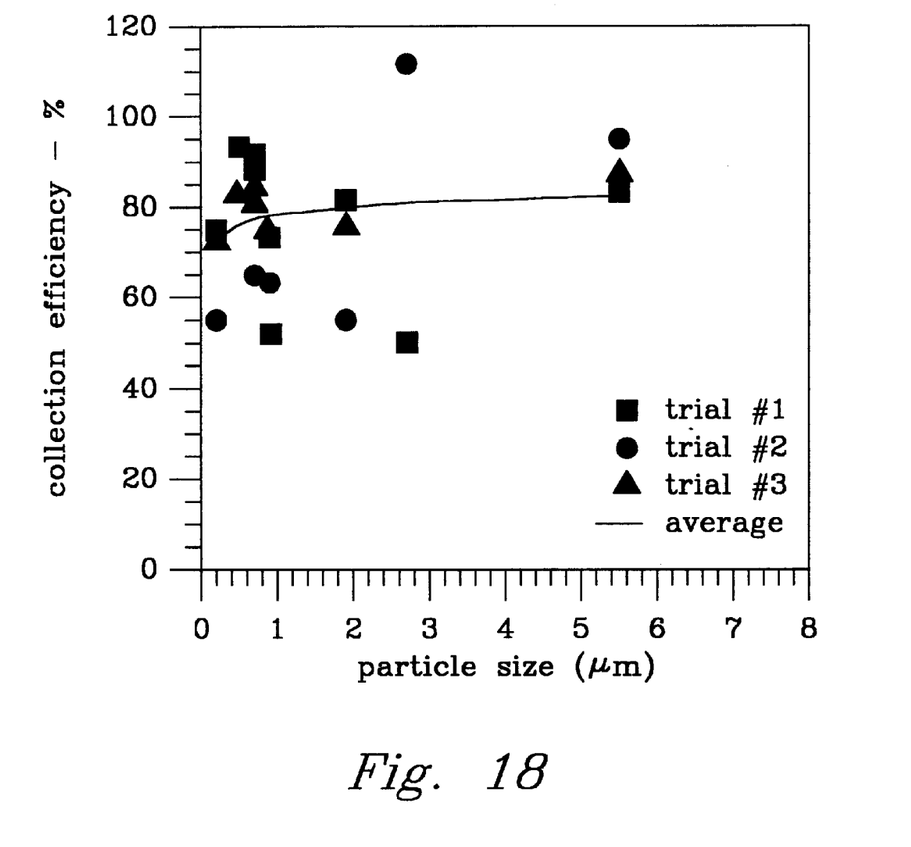

RESULTS: When fluorescent particles were left in the device and photographed, a much greater fluorescence is observed in the passageway from the aperture 156 to the collection component than on the "virtual impact", or concave, surfaces 152, indicating the efficiency of separation of the device. The results of this initial device (FIG. 18), which was not optimized for throughput or separation efficiency, show that in excess of 80% of almost all particle sizes can be expected, and with optimization, this is expected to increase to an excess of 90%. The pressure drop measured across the device was approximately 4" of water.

A preferred and various alternative embodiments of the present invention have been disclosed in detail. It will be appreciated by those of skill in this art that numerous improvements or modifications may be made to the invention without departing from the spirit and scope of the invention. Accordingly, the scope of the invention should be determined solely by reference to the scope of the appended claims.

We claim:

1. An apparatus for separation and concentration of particulate matter from a fluid stream, comprising:
    a. an inlet component through which the fluid stream enters the apparatus;
    b. a separation plate comprising a plurality of projections, each having a concave virtual impact surface;
    c. each of said projections defining an aperture therethrough through which a minor portion of the fluid stream and a major portion of the particulate matter are directed;
    d. each of said apertures defining a first terminus of a passageway extending through said projection and said separation plate, each of said passageways extending at an acute angle with respect to said separation plate and terminating in a second terminus;
    e. a collection component in fluid communication with each of said second termini to aggregate said minor portion of the fluid stream containing a major portion of the particulate matter; and
    f. a fluid outlet to exhaust a major portion of the fluid stream containing a minor portion of the particulate matter.

2. The apparatus of claim 1, wherein the aperture is provided at the apex of the concave virtual impact surface.

3. The apparatus of claim 2, wherein each of the projections is provided with a pair of opposing concave surfaces, one of said concave surfaces in an upstream direction and one of said surfaces in a downstream direction.

4. The apparatus of claim 2, wherein the plurality of projections are arranged in rows adjacent one another with a fluid passageway defined between adjacent projections such that a minor portion of the fluid stream passes through said aperture and a major portion of the fluid stream passes in said fluid passageways.

5. The apparatus of claim 4, wherein axes of apertures and axes of fluid passageways of one row of projections are offset from those axes of an adjacent row, such that axes of passageways of one row are aligned with axes of apertures of an immediately adjacent downstream row.

6. The apparatus of claim 4, wherein the plurality of rows of projections are arranged adjacent one another such that fluid flow through a fluid passageway between adjacent projections of an upstream row is directed to the aperture of the projection of a downstream row.

7. The apparatus of claim 6, wherein said plurality of rows of projections are arranged with progressively smaller dimensions of the concave surfaces and apertures such that fluid flow increases through the device and successively smaller particulate matter is removed from the device as fluid flows therethrough.

8. The apparatus of claim 2, wherein a leading edge surface of each of the projections is provided in a convex shape in the direction of the advancing fluid stream with said concave virtual impact surface at the apex of the convex shape.

9. The apparatus of claim 2, wherein said projections are arranged in a spiral pattern with each of said apertures directed to a central plenum to aggregate the separated particulate matter in a single concentrated fluid stream.

10. The apparatus of claim 1, wherein the fluid stream comprises an air stream.

11. The apparatus of claim 10, wherein the particulate matter is an aerosol selected from the group consisting essentially of chemical warfare agents, biological warfare agents, infectious or disease causing organisms, industrial pollutants, radioactive particles, toxic vapors illegal drugs or their precursors.

12. The apparatus of claim 1, wherein the fluid stream comprises a liquid stream.

13. The apparatus of claim 1, wherein the collection component comprises a liquid through which the minor portion of the fluid stream with a major portion of the particulate matter therein is directed.

14. The apparatus of claim 1, wherein laminar flow of particulate matter through the device reduces impacts between the particulate matter and the projections.

15. The apparatus of claim 1, which is selectively configured so as to separate and collect particulate matter having a diameter on the order of microns.

16. An apparatus for separating particulate matter from a gaseous stream, comprising:
   a. a gaseous stream intake plate including a gas intake plenum and a plurality of grooves, said intake plate further defining longitudinal troughs therein;
   b. a particle separation plate coupled to said air intake plate to receive the gaseous stream therefrom directed through said grooves, said particle separation plate including a plurality of projections arranged in longitudinal rows, said rows being adapted to interfit with the longitudinal troughs defined in the intake plate when the separation plate and the intake plate are coupled together, each projection defining a concave virtual impact surface that faces in the general direction of the advancing gaseous stream, each concave virtual impact surface defining an aperture therethrough, each aperture defining a first terminus of a passageway, each of said passageways extending through said projection and said separation plate and terminating in a second terminus; and
   c. a particle collection plate including at least one channel for collecting particles therein, the channel being fluidly communicated with each of said second termini of said passageways so that the aperture of each projection interconnects with the channel in said particle collection plate through said passageway.

17. The apparatus as recited in claim 16, wherein said projections have a geometric shape selected from the group consisting of butterfly, haystack, tab, and crescent shapes, and combinations thereof.

18. The apparatus as recited in claim 16, wherein said concave virtual impact surface that faces in the general direction of the advancing gaseous stream is defined within a surface that has a shape selected from the group consisting of convex and concave shapes.

19. The virtual impactor as recited in claim 16, further comprising a downstream aperture on each of said first projection.

20. The apparatus of claim 16, wherein said channel is filled with a liquid for collecting particles therein.

21. The apparatus of claim 16, which is selectively configured so as to separate and collect particulate matter having a diameter on the order of microns.

22. A micro-machined virtual impactor apparatus for separation of particulate matter from an air stream for detection and analysis, comprising:
   a. an air inlet component through which a quantity of air with particulate matter therein enters the apparatus;
   b. a separation component comprising a plurality of projections arranged in adjacent rows, said rows being arranged generally perpendicular to the direction of flow of the air stream, the individual projections of each row being offset from the individual projections of the adjacent downstream row;
   c. each of said individual projections having
      (i) a convex profile presented to the movement of the air stream,
      (ii) a fluid passageway between adjacent projections through which a major portion of the air stream is directed,
      (iii) a concave virtual impact surface at the apex of the convex profile, said virtual impact surface defining an aperture therein, and
      (iv) a passageway extending through the projection from said aperture to a second terminus, said passageway being arranged at an acute angle with respect to a plane defined by said rows of projections; and
   d. a collection component to receive a minor portion of the air stream passing through said apertures.

23. The apparatus of claim 22, wherein a minor portion of the air stream and a major portion of the particulate matter are directed into the apertures and thence to the collection component wherein the particulate matter is separated therefrom.

24. The apparatus of claim 22, wherein a dead air space is created within the concave portion of the virtual impact surface, such that a reduction in air velocity induces a major portion of the particulate matter to settle from the air stream and be collected adjacent the concave portion, and thereafter directed into the aperture with a minor portion of the air stream.

25. The apparatus of claim 24, wherein the minor portion of the air stream entering the aperture comprises from about 5% to about 40% of the air stream exposed to an individual projection, and the major portion of the particulate matter entering the aperture comprises from about 60% to about 99% of the particulate matter in the air stream.

26. The apparatus of claim 22, wherein said rows of projections are arranged in a spiral pattern and said apertures are all interconnected as said collection component in the form of a master plenum for collection of the particulate matter.

27. A method of separating particulate matter from a fluid stream, comprising the steps of:
   a. directing the fluid stream toward a plurality of individual virtual impact devices in the form of projections, each of said projections defining a concave virtual impact surface with an aperture disposed adjacent said concave virtual impact surface;
   b. creating a stagnant air zone within said concave virtual impact surface;
   c. directing a minor portion of said fluid stream into the concave portion of the virtual impact surface, and directing a major portion of the fluid stream around an individual virtual impact surface;
   d. permitting a major portion of the particulate matter to be entrained in the minor portion of the fluid stream directed adjacent the concave virtual impact surface, such that the particulate matter and the minor portion of the fluid stream enter the aperture;
   e. directing the major portion of the particulate matter entrained in the minor portion of the fluid stream for collection at an acute angle with respect to the direction of the fluid stream directed toward the plurality of virtual impact devices at step (a); and
   f. collecting the minor portion of the fluid stream such that the particulate matter therein may be analyzed.

28. The method of claim 27, further comprising the step of arranging the individual projections in adjacent rows arranged generally perpendicular to the flow of the fluid stream.

29. The method of claim 27, further comprising the step of arranging the individual projections in a spiral arrangement, such that the spiral configuration acts as a virtual centrifuge to separate and relatively larger particulate matter from the fluid stream.

30. The method of claim 27, wherein the major portion of the particulate matter to be collected has a diameter on the order of microns.

* * * * *

UNITED STATES PATENT AND TRADEMARK OFFICE
CERTIFICATE OF CORRECTION

PATENT NO. : 6,010,554
DATED : January 4, 2000
INVENTOR(S) : J.G. Birmingham et al.

It is certified that error appears in the above-identified patent and that said Letters Patent is hereby corrected as shown below:

Column 10,
Line 54, (Claim 11, line 5) after "toxic vapors" insert -- , --

Column 11,
Line 35, (Claim 19, line 1) "virtual impactor" should read -- apparatus --
Line 37, (Claim 19, line 3) "projection" should read -- projections --

Column 12,
Line 61, (Claim 29, line 4) "separate and" should read -- separate any --

Signed and Sealed this

Eighteenth Day of September, 2001

Attest:

NICHOLAS P. GODICI
Attesting Officer
Acting Director of the United States Patent and Trademark Office